United States Patent [19]

Henrie

[11] Patent Number: 4,729,763
[45] Date of Patent: Mar. 8, 1988

[54] CATHETER FOR REMOVING OCCLUSIVE MATERIAL

[76] Inventor: Rodney A. Henrie, 136 E. Third St., Mount Carmel, Pa. 17851

[21] Appl. No.: 871,473

[22] Filed: Jun. 6, 1986

[51] Int. Cl.$^4$ ............................................. A61B 17/32
[52] U.S. Cl. ..................................... 604/22; 128/305
[58] Field of Search ................... 604/22, 27, 35, 39, 604/43, 53, 101, 113, 267; 128/304, 305, 311, 399–401

[56] References Cited

U.S. PATENT DOCUMENTS

| 910,859 | 1/1909 | Reusch | 604/113 |
|---|---|---|---|
| 3,320,957 | 5/1967 | Sokolik | 128/311 |
| 3,805,793 | 4/1974 | Wright | 604/22 |
| 4,167,943 | 9/1979 | Banko | 128/305 |
| 4,203,444 | 5/1980 | Bonnell et al. | 604/22 |
| 4,274,414 | 6/1981 | Johnson et al. | 128/305 |
| 4,445,892 | 5/1984 | Hussein et al. | 604/101 |
| 4,631,052 | 12/1986 | Kensey | 604/22 |
| 4,649,919 | 3/1987 | Thimsen et al. | 604/22 |

FOREIGN PATENT DOCUMENTS

| 665908 | 5/1979 | U.S.S.R. | 128/304 |
|---|---|---|---|
| 3019115 | 12/1981 | U.S.S.R. | 128/303 R |

OTHER PUBLICATIONS

Archives of Surgery, Jul. 1972, vol. 105, pp. 79–82, "Complications of the Use of the Fogarty Balloon Catheter" by Dr. Edward A. Dainko.
Cardiovascular News, McMahon Publishing Co., Feb. 1986, pp. 1 and 4.

*Primary Examiner*—Stephen C. Pellegrino
*Assistant Examiner*—Ralph Lewis

[57] ABSTRACT

A catheter is provided for removing occlusive material from the stenosis of a blood vessel. The catheter comprises a flexible outer tube and a flexible rotatable inner tube which is concentric with and spaced radially inward of the outer tube forming a channel between the two tubes through which liquid is supplied to the vessel. Hollow cutting means are connected to the rotatable inner tube and are positioned within the free end of the catheter to avoid contact of the cutting means with the blood vessel. The fluid flowing in the channel between the tubes to the blood vessel is capable of dissolving and dislodging the stenosis material where it is entrained in the fluid. The entrained stenosis material is cut into smaller pieces and withdrawn as the fluid is sucked through the hollow cutting means and out through the inner tube. The catheter is additionally provided with means for viewing the condition of the blood vessel interior throughout the procedure.

11 Claims, 10 Drawing Figures

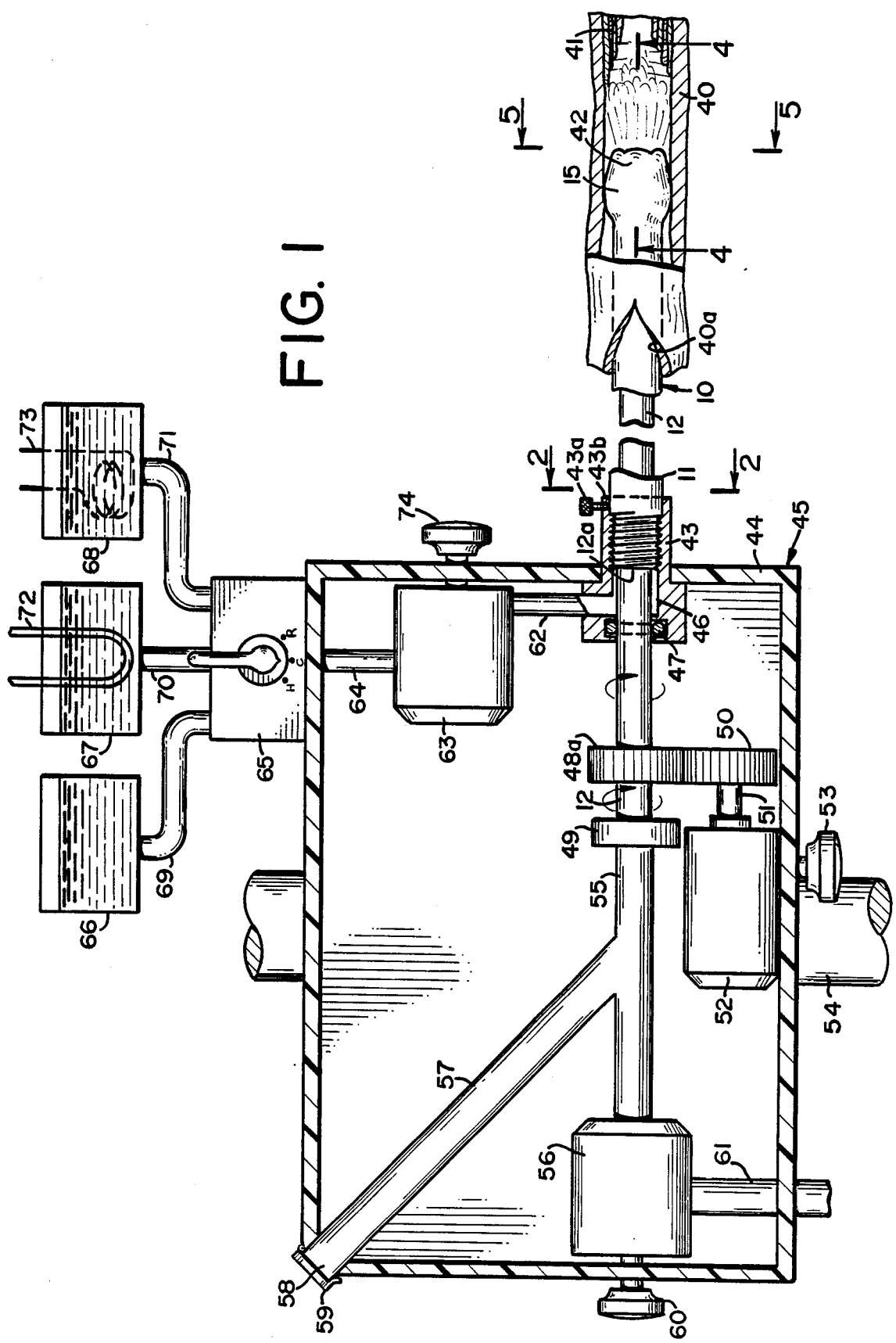

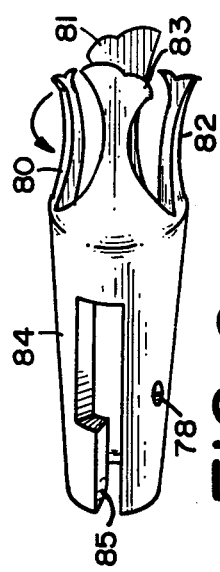
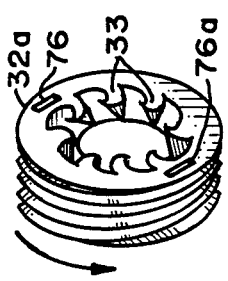
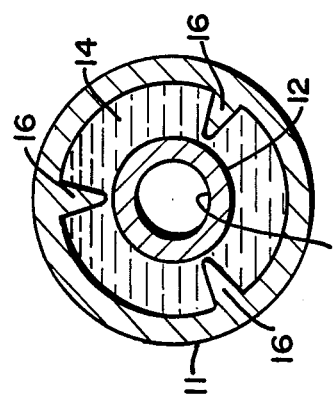
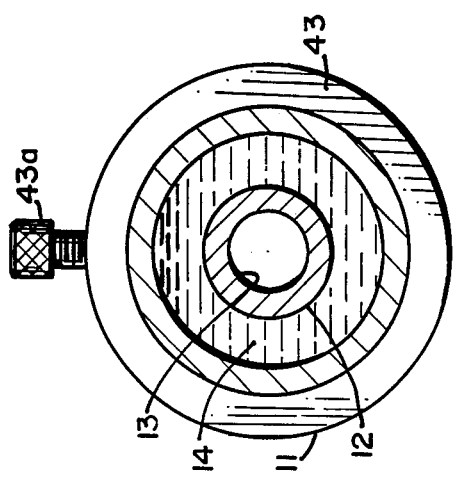
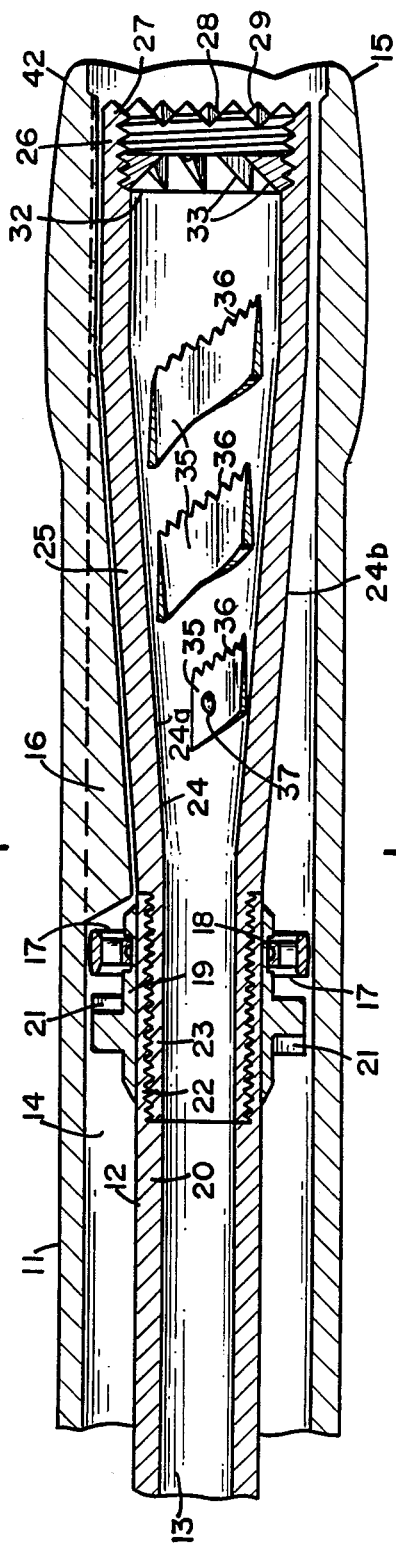

CATHETER FOR REMOVING OCCLUSIVE MATERIAL

CROSS-REFERENCES TO RELATED APPLICATIONS

None.

BACKGROUND OF THE INVENTION

1. The field of the invention comprises catheters for removing occlusive material from blood vessels.

2. Description of the Prior Art. In a conventional catheter for removing occlusive material such as plaque and emboli, a stylet wire covered with a soft flexible tubing is joined with a luer lock connection to a symmetrically inflatable latex balloon. The balloon has a softer distal tip which is inserted past the stenosis of the blood vessel with said balloon deflated. The balloon is then inflated by means of air pressure through said tubing, and the catheter is then retracted, accumulating occlusive materials before the posterior portion of the balloon during the withdrawal process.

"Over a seven-year period, during which time approximately 500 such balloon tipped catheters have been used in surgical procedures, six complications have been recognized. These were the disruption of the posterior tibial artery, perforation of the popliteal artery, breaking off of the catheter tip in the profunda femoris artery, disruption of an intra-hepatic bile duct, and two disruptions of saphenous vein in situ grafts while rendering valves incompetent." (Reprinted from the Archives of Surgery, July 1972, Vol. 105, American Medical Association, pp. 79-82)

The described types of arterial injuries, including arterial rupture, arterial perforation, and intimal wrinkling, often lead to intimal disruption. Risk of such arterial injuries is greatly lessened with this invention by the absence of a distal tip. Intimal wrinkling would be minimal or non-existent upon insertion. Chances of damage to blood vessels of sufficient size to accept this invention would be greatly lessened and extremely remote. The introduction of lubricants for dissolving or entraining the cut occlusive material or debris, a fiber optic light and lens, and healing agents in solution or suspension through said catheter are capabilities not present in existing catheters.

Another catheter equipped with a high speed, air pressure driven rotary blade employs a guidewire which passes through the lumen, or bore, of the catheter and across the stenosis. The rotating cutter is thereby moved forward to dissect the occlusive plaque. No means is provided for removing the reduced occlusive material from the blood vessel. This procedure is described in Cardiovascular News, McMahon Publishing Co., February 1986, pp. 1 and 4.

SUMMARY OF THE INVENTION

The catheter of the invention is designed to remove occlusive material from the stenosis of a blood vessel. It has a free end for insertion in the blood vessel. It comprises a flexible outer tube and a flexible, rotatable inner tube which is concentric with and spaced radially inwardly of the outer tube. A channel is formed between the tubes. Hollow cutting means are connected to the rotatable inner tube and are positioned within and short of the open free end of the catheter to avoid contact of the cutting means with the blood vessel. Means are also provided for flowing liquid through the channel between the inner and outer tubes, then through the free end of the catheter, and then through the hollow cutting means and bore of the inner tube, thereby to entrain subdivided occlusive material in the liquid and to remove the same from the blood vessel. Various liquids can be used and can be heated or cooled by conventional means before being introduced into the channel. Means are also provided for applying a vacuum to the lumen or bore of the inner tube.

In one modification the cutting means is in the form of a spirally-shaped blade having cutting edges that are serrated.

In another modification the cutting means is in the form of a plurality of cutting blades of unequal length disposed circumferentially of the inner tube, the longest blade being disposed inwardly of the free end of the catheter to avoid contact of the blades with the blood vessel.

In a preferred embodiment, applicable to either modification, means are provided for rotatably supporting the inner tube within the outer tube at a place adjacent and spaced from the free end of the catheter.

BRIEF DESCRIPTION OF THE DRAWINGS

The invention is illustrated in the following drawings, which are diagrammatic, and in which FIG. 1 is a side elevational view of the device, partially sectioned and partially broken away to show the interior construction;

FIG. 2 is a cross section view along line 2—2 of FIG. 1;

FIG. 3 is a sectional view along line 3—3 of FIG. 4, with portions omitted for the sake of clarity;

FIG. 4 is an enlarged sectional view along line 4—4 of FIG. 1;

FIG. 9 is a perspective view of the cutter endpiece of FIG. 8; and

FIG. 10 is a perspective view of the threaded toothed disc shown in cross section in FIG. 8.

DESCRIPTION OF THE SPECIFIC EMBODIMENTS

Figure 6:
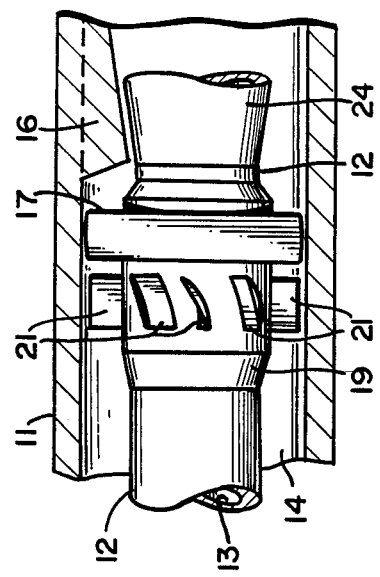
FIG. 6 is an enlarged partial sectional view of a detail of FIG. 4 comprising a means for rotatably supporting the inner tube of the device within the outer tube at a place spaced from the free end; with spiral cutting means omitted for the sake of clarity.

Referring to FIGS. 1-4, the catheter 10 of the invention comprises a flexible outer tube 11 and a flexible rotatable inner tube 12 that is concentric with and spaced radially inwardly of the outer tube. Tube 12 has a central lumen or bore 13. Between the two tubes is an axially extended channel or space 14.

As shown in FIGS. 1 and 4, the catheter 10 has a slightly enlarged free end 15, inwardly of which are a plurality of circumferentially spaced ribs or extensions 16, note FIGS. 3 and 4, which extend radially inwardly toward the outer tube, and which extend longitudinally from said free end to a spoked wheel, shown in FIG. 4, which is free to rotate in an annular groove 18 formed in the short annular sleeve or collar 19, also note FIG. 6. The sleeve 19 is press-fitted to the end portion 20 of inner tube 12, is rotatable therewith, and is provided with integral fins or blades 21.

The described grooved collar, fins, and spoked wheel arrangement comprise a means for rotatably supporting the inner tube 12 in the outer tube 11, and the spoked wheel also acts as a bearing to reduce friction. One or more of such means can be disposed at a place spaced from the free end of the catheter.

Figure 7:
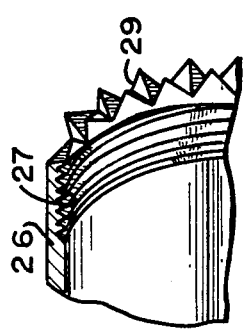
FIG. 7 is a partial view of the cutting end of the endpiece of FIG. 4 showing the cutting teeth in more detail.

As shown in FIG. 4, the end portion 20 of tube 12 is internally threaded at 22 to receive a correspondingly threaded inner end portion 23 of endpiece 24, the latter having a diameter which gradually increases, as at 25, and which terminates in end section 26 having an internally threaded outer end portion 27. The end edge 28 of such portion 27 is provided with cutting means in the form of teeth 29, illustrated in FIGS. 4 and 7, which as shown have three sides but which may also have a variable number of sides. A threaded disc 32 is threadedly engaged in the end portion 27 and is provided with cutting means in the form of curved teeth 33. Other conventional ways of securing the disc may be employed.

Disposed inside the lumen or bore 24a of the tapered endpiece 24 is another cutting means in the form of a single spirally shaped member 35 having a serrated or tooth-shaped edge 36 which is disposed towards the free end of the catheter. The member 35 is secured to endpiece 24 as by conventional fasteners such as rivets, one of which is seen at 37. As shown, the spiral member 35 has a decreasing diameter to conform to the taper of the endpiece 24.

In FIG. 1 a blood vessel 40 is shown in the lumen or bore of which the catheter is operatively disposed, and at 41 is shown the occlusive material, plaque, atheroma, emboli, etc. to be removed. To avoid damage to the vessel by the various described cutting means, there are provided means in the form of the outwardly extending annular end portion 42, also note FIG. 4, of the catheter to prevent contact between the blood vessel and cutting means.

At the end remote from free end 15 the catheter is connected to and supported by an internally threaded coupling means 43 which in turn is supported on the wall 44 of housing or case 45. A locking screw 43a is threaded through coupling wall 43b and when tightened secures the outer tube 11. Other conventional locking means may be used to secure tube 11.

As noted, one of the functions of coupling means 43 is to support the catheter at a point remote from the free end 15. The outer tube 11 of the catheter terminates within the coupling means 43, while the inner tube 12 continues through liquid chamber 46, then through O-ring seal 47 and on through the bore of a gear 48a to terminate in a bearing 49.

Meshing with a gear 48a is a gear 50 rotatable by shaft 51 which is driven by a motor shown at 52. By such means the inner tube and the cutting means are rotated. At 53 is a control means for the motor, and at 54 is shown a support that is movable to adjust the position of the entire apparatus. To the left of bearing 49 is a stationary hollow tube 55, which communicates with inner tube 12 and also with vacuum pump 56, and by such means a vacuum is applied to the said inner tube. A hollow tube 57, the function of which will be described later, is connected to tube 55; it has a free open end 58 which extends through the housing 45 and which is closed by a hinged cap 59. Control means for the pump are indicated at 60, while at 61 is a disposal tube for the emission of occlusive material debris removed by the pump.

Returning to chamber 46, a tube 62 connects it to a pump 63 which draws liquid through tube 64 and selecting valve 65 from any one of liquid reservoirs 66, 67, and 68, each having a connection 69, 70, 71, respectively, to the valve. Reservoir 67 is provided with cooling means 72, shown as a cooling coil, while reservoir 68 has the heating means 73 in the form of a heating coil. A control means for pump 63 is indicated at 74.

It will be understood that the outer tube 11 which terminates inside the coupling means 43 is open at its end 12a to allow liquid from chamber 46 to flow into the channel 14 between the inner and outer tubes 12 and 11.

The operation of the invention may be described briefly as follows:

After standard surgical preparation of the body area, clamps (not shown) are positioned before and beyond the constricted area of the blood vessel 40 containing occlusive material 41 and its branchings. An incision 40a is then made into the blood vessel 40 some space before the blockage.

Figure 5:
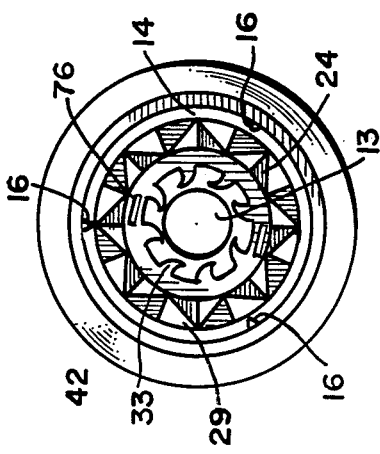
FIG. 5 is an enlarged sectional view along line 5—5 of FIG. 1.

The Teflon coated and conventionally lubricated free end 15 of the catheter is then inserted through the incision and is forward gently until it encounters the occlusive material. The liquid control knob 74 is then opened and set to activate and adjust pump 63 and to allow a given quantity of liquid from liquid reservoir 68 to flow through the connecting tube 71, liquid selection valve 65, connecting tube 64, pump 63, connecting tube 62, then into liquid chamber 46 and on through space 14 between the outer tube 11 and inner tube 12 of the catheter 10 to emerge from channel opening 14 of FIG. 5 in the free end 15. The narrow, circular propelled stream of heated liquid containing cholesterol emulsifiers is designed to enter between the layers of occlusive material (plaque, atheroma, or emboli), dissolving certain components such as cholesterol (having a melting point of 106 degrees Fahrenheit or 41 degrees Celsius) and to separate the layers of occlusive material from each other and from the inner wall of the blood vessel.

As soon as the melting of the heated and treated occlusive material begins to occur, the rotating action of the inner tube 12 is activated by control knob 53, and the vacuum action within inner tube 12 is initiated by control knob 60. The rotating action sets in motion the cutting means of the inner tube's endpiece 24 to reduce the size of the more solid pieces. The vacuum action then draws the entrained waste material off by means of suction created in the bore 13 of inner tube 12 by vacuum pump 56.

The catheter is advanced manually until all the occlusive material is removed or until an assessment of the situation within the blood vessel is desired. When an assessment is in order, the liquid flow, inner tube 12 rotation and vacuum action are stopped. The hinged cap 59 at the free end 58 of tube 57 is then opened and a fiber optic light and lens (not shown) are inserted past the cutting means and beyond the free end 15 to determine if further advancement of the catheter 10 is required. It should be noted that insertion and retraction of the fiber optic light and lens through the inner tube 12 of the catheter eliminates any irritating or abrasive contact with the inner wall of the blood vessel 40.

A chilled liquid from reservoir 67 is provided through valve 65 for those times when a contrast of rapid chilling of the occlusive material would be deemed advisable to congeal or otherwise alter the conditions of the debris, or to cleanse the inner tube 12 as for example before the insertion of the fiber optic unit (not shown).

When all occlusive material has been removed, a third liquid may be released from reservoir or chamber 66 through valve 65 as the catheter 10 is being retracted. This liquid may be allowed to fill the entire clamped off area since this liquid contains cleansing and healing agents which may soak into the inner wall of the blood vessel 40 until the enlarged free end 15 of the catheter 10 is withdrawn to a short distance within the incision. The liquid pressure control 74 which controls pump 63 is then shut off. A period of waiting may ensue to enhance absorption. The vacuum pump 56 may then be activated to draw off the excess liquid. The vacuum pump control 60 is then shut off and the catheter 10 is removed from the incision. The healing agents such as certain vitamins and medicines which remain as residue on the inner wall of the blood vessel will continue to soak into the lining of the inner wall until the incision 40a is closed and until the clamps (not shown) are released.

Considering some of the structures of FIG. 1 in more detail, the liquid chamber 46 provides a means whereby the liquid passing through tube 62 may flow completely around inner tube 12 to fill channel 14. Chamber 46 is comprised of a metal or plastic container with an opening in the top to receive tube 62. The chamber 46 allows the liquid to flow into coupling means 43 and channel 14 (FIGS. 2 and 4). A third opening on the opposite, inward side of chamber 46 allows inner tube 12 to extend through O-ring seal 47 which contains the liquid within chamber 46 but allows for the rotation of inner tube 12.

Bearing 49 serves to connect the rotating inner tube 12 with the stationary tube 55. This connection also allows for the transmission of the suction action of the vacuum pump 56 to be maintained over the entire length of the apparatus from vacuum pump 56 to the enlarged free end 15 of the catheter 10. The bearings may be of a conventional ball or roller shape and housed in such a manner as to allow tube 55 to the left of bearing 49 to remain stationary while the attached inner tube 12 on the right side of bearing 49 is free to rotate.

Reservoir 68 contains a liquid heated by means of a heating coil 73 submerged in the liquid.

Reservoir 67 contains a liquid cooled by means of a chilled gas or solution flowing through a tube 72 submerged in the liquid.

The control means 74 for liquid pump 63 is designed to control conventionally the revolutions per minute of and pressure exerted by electric pump 63 upon the liquid which said pump is thrusting through tube 62, liquid chamber 46, coupling means 43, and channel 14.

The control means 53 for motor 52 is designed to control by conventional means the revolutions per minute of motor shaft 51 and attached gear 50, which in turn rotates gear 48a and inner tube 12. It is to be understood that such rotating motion is transmitted by means of inner tube 12 for rotating and controlling the attached rotatable endpiece 24 with its various cutting means 29, 33, and 36. Other conventional means for transferring rotating motion from motor 52 to inner tube 12 may be used.

The control means 60 for vacuum pump 56 is designed to control by conventional means the strength or amount of suction to be created inside tube 55 and through inner tube 12 to the endpiece 24 opening. It is to be understood that the same vacuum pump 56 also provides thrust for occlusive material debris to be discharged from disposal tube 61.

The fiber optic light and lens unit (not shown) recommended for use with this invention is the conventional variety with an outside diameter of 2 millimeters (or 5/64 of an inch). The largest fiber optic unit which could be inserted and pass through the smallest lumen or bore of inner tube 12 of larger models would be approximately 3 millimeters (or 1/8 of an inch) in diameter. It will be understood that the fiber optic unit used should be sufficiently long to extend through the entire length of the housing case 44 and catheter 10 and beyond the opening of the enlarged free end 15 a short distance to be able to allow the operators of the invention to assess the internal conditions of the blood vessel. Since the insertion and retraction of the fiber optic unit occurs inside the non-rotating inner tube 12 of catheter 10 there will be no additional disturbance to the inner lining of the blood vessel 40 being treated.

One liquid containing natural cholesterol emulsifiers is lecithin and/or grain alcohol in a water base. It can be heated up to 110 degrees Fahrenheit to 130 degrees Fahrenheit (43–57 degrees Celsius) for the purpose of dissolving the cholesterol and fatty portions of the occlusive materials when said liquid is discharged (under pressure) through channel 14.

A cooling liquid may simply be clear water or physiological saline solution chilled within a range from 65 degrees Fahrenheit to 35 degrees Fahrenheit (18 to 2 degrees Celsius). This liquid may be employed to congeal cholesterol and fatty particles in the blood vessels, to aid in the flushing of the loosened occlusive material 41 within the blood vessel 40, and to ease and enhance the removal of the occlusive material through inner tube 12 by means of a vacuum. This liquid may also be used when catheter 10 is stationary and inner tube 12 is not rotating to flush and cleanse inner tube 12 prior to the insertion of the fiber optic light and lens (not shown).

A third liquid containing healing agents such as, but not limited to, vitamins C and E may be inserted into the unclogged but still clamped blood vessel through channel 14 upon the catheter's retraction. This liquid may have a temperature range from 98 degrees Fahrenheit to 120 degrees Fahrenheit (37 to 49 degrees Celsius) and may be allowed to fill the entire clamped area to soak into the inner wall of the blood vessel until the enlarged free end 15 of catheter 10 is withdrawn to a short distance within the incision 40a. The vacuum pump may then be activated to draw off the excess liquid.

Since the fiber optic light and lens unit may be as low as 2 mm (5/64 of an inch) in diameter, the lumen or bore 13 of inner tube 12 may be approximately 2.5 mm (1/10 of an inch) in diameter (to allow for passage of the fiber optic unit through said lumen or bore 13). If surgical steel or titanium alloy is used as the construction material of both catheter 10 and inner tube 12, then the thickness of the catheter and inner tube walls may be as low as one millimeter (20/1000 of an inch) or even smaller. The outside diameter of the enlarged free end 15 of a catheter may be as low as 6.5 mm to 9.5 mm (1/4 to 3/8 of an inch).

Other metals or metal alloys possessing characteristics of firmness and flexibility are also suitable construction materials for catheter 10 and inner tube 12. Plastic material, preferably colorless and of the heat-hardening variety, may also be selected as suitable construction material for both catheter 10 and inner tube 12. Applicable plastics include but are not limited to: acrylic resins, nylon, hexamethylene adipamide resins, polyethylenes, polyesters, polystyrenes, and polypropylenes.

Figure 8:
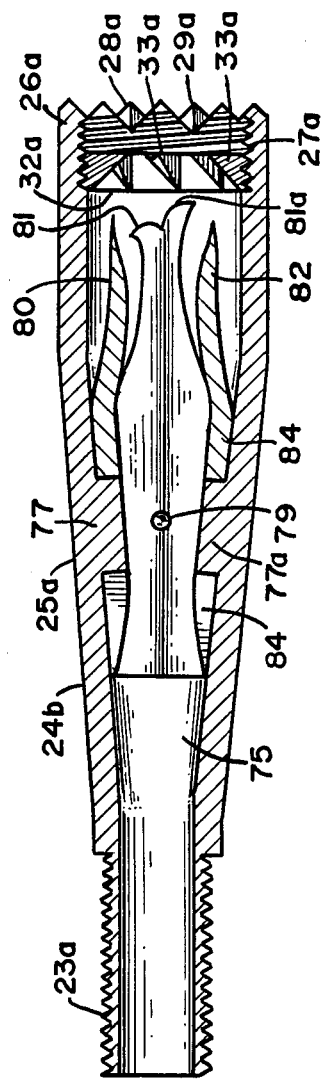
FIG. 8 is a sectional view similar to FIG. 4, but showing an alternative construction of the cutting means.

The modified cutting means shown in FIGS. 8 and 9 is comprised of the endpiece 24b having an externally threaded end portion 23a to be engaged by the end portion 20 (FIG. 4) of inner tube 12 (FIG. 4) which is internally threaded. Endpiece 24b has a diameter which gradually increases as at 25a and which terminates in end section 26a having an internally threaded outer end portion 27a. The end edge 28a of such portion 27a is provided with cutting means in the form of teeth 29a which as shown in FIG. 8 have three sides but which may also have a variable number of such sides. A threaded disc 32a is threadedly engaged in the end portion 27a and is provided with cutting means in the form of curved teeth 33a. Any conventional means of securing the disc may be employed.

Disposed inside the tapered endpiece 24b is another cutting means in the form of a hollow, tubular body having a plurality of slightly curved cutting blades 80, 81, and 82 of unequal length disposed circumferentially. Each blade has a respective cutting edge 81a disposed on the end portions thereof as shown on blade 81. The tubular body 84 has two slots. One slot 85 is shown in FIG. 9. A hole 78 in the tubular body is positioned to align with a corresponding hole (not shown) in the endpiece 24b to receive a rivet 79 of FIG. 8.

To assemble the tubular body 84 in the central bore 75 of endpiece 24b, the two slots (one shown at 85) must be aligned to slide past two inward extending bars 77 and 77a which are integral with endpiece 24b. A counterclockwise motion is required to tubular body 84 to fix the inward extending bars 77 and 77a in proper position and to align holes (one is shown at 78 in FIG. 9) in the tubular body 84 with holes (not shown) in the endpiece 24b to receive a rivet in each hole as shown at 79 of FIG. 8. The endpiece 24b is now ready to receive the threaded disc 32a for the complete assembly of endpiece 24b. Two slots or grooves 76 and 76a of FIG. 10 allow for the tightening and loosening of threaded disc 32a.

A further advantage of the invention lies in the removability of cutters 32 by virtue of having a removable endpiece 24. When cutting means including the toothed disc 32 become dull, said cutting means may be removed for sharpening. It should also be noted that with the counterclockwise motion of the inner tube's rotation, the result is a constant tightening of the inner tube 12 to the enlarged threaded endpiece 24 and of endpiece 24 to the threaded disc 32.

Additional advantages of this invention lie in the means to provide liquids of various compositions and temperatures to the occluded area both for the loosening of the occluded material and for the cleansing of the area for visual inspection by means of a fiber optic light and lens. The insertion and retraction of the fiber optic light and lens through the central lumen or bore of the inner tube prevents disturbance to the blood vessel.

A further advantage of this catheter lies in the means of removing or withdrawing the dislodged and reduced occlusive materials from the blood vessel by the use of vacuum suction through the central lumen or bore of the inner tube.

Means are also present to use the flow of liquids to rotatably support the inner tube and thereby reduce the chances of over-twisting said inner tube.

The invention has the advantage of rapid and positive action in the removal of occlusive material from the stenosis of a blood vessel.

An alternative embodiment of the invention eliminates the mechanical driving means comprising the motor 52, control 53, shaft 51, and gears 50, 48a. In this embodiment, the energy of the fluid flowing through the channel 14 would impinge upon the fins 21 of sleeve 19 in a turbine-like manner thereby imparting rotary motion to the sleeve and thereby to the inner tube 12. Additional sleeves and fins may be affixed to the inner tube 12 in a spaced apart relationship for enhancing the rotarty motion wherein the first sleeve is disposed a short distance inwardly from the enlarged free end 15 of the catheter.

The stationary tube 55 and the inner tube 12 can be configured to permit cooperative bearing action thereby eliminating the bearing 49.

I claim:

1. A catheter useful to remove occlusive material from a blood vessel and having a free end for insertion in said vessel,
   comprising a flexible outer tube,
   a flexible rotatable inner tube having a central lumen or bore and being concentric with and spaced radially inwardly of said outer tube, thereby forming at least one axially extending channel between said tubes, hollow cutting means for said occlusive material connected to said inner tube and rotatable therewith, said cutting means being disposed within and short of said free end of the catheter,
   means for rotating said inner tube and said cutting means, thereby to cut said occlusive material and to reduce the same to a subdivided form, said inner tube being immovable in an axial direction relatively to the outer tube,
   means for flowing a liquid through said channel, through said free end of the catheter, and through said hollow cutting means, said liquid entraining the subdivided occlusive material, said channel and said lumen or bore being continuously open from end to end thereof thereby to permit entrained occlusive material to be removed from said blood vessel through said lumen or bore of the inner tube,
   and means for applying a vacuum to said inner tube and hollow cutting means to promote removal of said subdivided occlusive material.

2. Device of claim 1 wherein means are present for rotatably supporting said inner tube within said outer tube adjacent said free end of the catheter.

3. Device of claim 1 wherein means are present for heating said liquid before introduction of the same to said channels, thereby to promote emulsification and dissolution of components of said occlusive material.

4. Device of claim 1 wherein said catheter has means for preventing contact between said cutting means and said blood vessel.

5. Device of claim 1 wherein said hollow cutting means comprises a spirally shaped blade having cutting edges that are serrated.

6. Device of claim 1 wherein said hollow cutting means comprises a plurality of cutting blades of unequal length disposed circumferentially of said inner tube, the longest of said blades being disposed inwardly of said free end of the catheter to avoid contact of the blades with said blood vessel.

7. Device of claim 1 wherein means are present for cooling said liquid before introduction of the same to said channels.

8. Device of claim 1 wherein means are provided for locking the outer tube against rotation.

9. Device of claim 1 wherein a third tube is provided in communication with said inner tube for allowing an assessment to be made of the condition of the blood vessel.

10. A catheter useful to remove occlusive material from a blood vessel and having a free end for insertion in said vessel, comprising a flexible outer tube, a flexible rotatable inner tube having a lumen or central bore and being concentric with and spaced radially of said outer tube, an axially extending channel between said tubes, hollow cutting means for said occlusive material connected to said inner tube and rotatable therewith, said cutting means being disposed inwardly of and short of said free end of the catheter to avoid contact of the blades with said blood vessel, means for rotatably supporting said inner tube adjacent said free end, said inner tube being immovable in an axial direction relatively to the outer tube, means for locking the outer tube against rotation, means for rotating said inner tube and said cutting means, thereby to cut said occlusive material and to reduce the same to a subdivided form, means for flowing a liquid through said channel, then through said free end of the catheter, and then through said hollow cutting means and said inner tube lumen or bore, said liquid entraining the subdivided material, said channel and said lumen or bore being continuously open from end to end thereof thereby to permit entrained occlusive material to be removed from said blood vessel, means for heating said liquid before introduction of the same into said channel, thereby to promote emulsification and dissolution of components of said occlusive material, and means for applying a vacuum to said inner tube and hollow cutting means to promote removal of said subdivided material.

11. Device of claim 10 wherein means are present for cooling said liquid.

* * * * *